(12) United States Patent
Hey et al.

(10) Patent No.: US 11,291,525 B2
(45) Date of Patent: Apr. 5, 2022

(54) MANDIBLE PROTRUSION SPLINT

(71) Applicant: HICAT GMBH, Bonn (DE)

(72) Inventors: Joachim Hey, Koenigswinter (DE); Daniel Gruenberg, Bonn (DE); Dirk Freyer, Cologne (DE)

(73) Assignee: HICAT GMBH, Bonn (DE)

( * ) Notice: Subject to any disclaimer, the term of this patent is extended or adjusted under 35 U.S.C. 154(b) by 158 days.

(21) Appl. No.: 16/487,434

(22) PCT Filed: Feb. 16, 2018

(86) PCT No.: PCT/EP2018/053924
§ 371 (c)(1),
(2) Date: Aug. 21, 2019

(87) PCT Pub. No.: WO2018/153789
PCT Pub. Date: Aug. 30, 2018

(65) Prior Publication Data
US 2019/0380814 A1    Dec. 19, 2019

(30) Foreign Application Priority Data
Feb. 23, 2017    (DE) ...................... 10 2017 103 722.5

(51) Int. Cl.
*A61F 5/56* (2006.01)
*A61C 7/08* (2006.01)
*A61C 7/36* (2006.01)

(52) U.S. Cl.
CPC .................. *A61C 7/08* (2013.01); *A61C 7/36* (2013.01); *A61F 5/566* (2013.01)

(58) Field of Classification Search
CPC ...... A61F 5/56; A61F 5/566; A61F 2005/563; A61C 7/08; A61C 7/36; A63B 71/085;
(Continued)

(56) References Cited

U.S. PATENT DOCUMENTS 1,654,479 A * 12/1927 Fenton ............... A44B 17/0005
 24/688
2,035,031 A * 3/1936 Von Koczian ..... A44B 11/2592
 24/595.1
(Continued)

FOREIGN PATENT DOCUMENTS

DE    20 2008 011 841 U1    12/2008
DE    10 2010 046 369 A1    3/2012
(Continued)

*Primary Examiner* — Camtu T Nguyen
(74) *Attorney, Agent, or Firm* — Norman B. Thot

(57) ABSTRACT

A mandibular protrusion splint includes a maxillary splint part and a mandibular splint part, each of which have a laterally attached joint pin, and joint rods which couple the splint parts together in a movable manner. Each joint pin comprises a shoulder facing the splint part, a head facing away from the splint part, and a neck arranged between the shoulder and the head. The shoulder and head cross sections are larger than a neck cross section. Each joint pin holds a joint rod. The joint rods have a collar at each end. Each collar surrounds the neck in a mounted state. The collar(s) and/or the head(s) have a flexibility which, upon an excessive application of a laterally directed force exerted via a joint rod, allows a yielding movement of the joint rod and then allows the collar to slip over the head of the joint pin without being destroyed.

8 Claims, 3 Drawing Sheets

(58) Field of Classification Search
CPC ........ A63B 2071/086; A63B 2071/088; A44B 1/04; A44B 17/00; A44B 17/0011; A44B 18/0038; A44B 18/0042; A44B 18/0061; A44B 18/0065
USPC ........................................................ 24/595.1
See application file for complete search history.

(56) References Cited

U.S. PATENT DOCUMENTS

| | | | | |
|---|---|---|---|---|
| 4,413,978 A | * | 11/1983 | Kurz | A61C 5/007 |
| | | | | 433/6 |
| 5,378,147 A | | 1/1995 | Mihailowitsch | |
| 6,109,265 A | * | 8/2000 | Frantz | A61F 5/566 |
| | | | | 128/848 |
| 10,201,450 B2 | * | 2/2019 | Vincent | A61F 5/566 |
| 2003/0207224 A1 | * | 11/2003 | Lotte | A61C 7/36 |
| | | | | 433/6 |
| 2009/0032030 A1 | * | 2/2009 | Callender | A61F 5/566 |
| | | | | 128/845 |
| 2011/0155144 A1 | | 6/2011 | Toussaint | |
| 2012/0073582 A1 | | 3/2012 | Kopp | |
| 2014/0335468 A1 | | 11/2014 | Dickerson | |
| 2015/0059766 A1 | * | 3/2015 | Frantz | A61F 5/566 |
| | | | | 128/848 |
| 2015/0216716 A1 | * | 8/2015 | Anitua Aldecoa | A61C 7/08 |
| | | | | 128/848 |
| 2018/0263806 A1 | * | 9/2018 | Toussaint | A61F 5/566 |
| 2020/0197214 A1 | * | 6/2020 | Frantz | A61F 5/566 |

FOREIGN PATENT DOCUMENTS

| | | |
|---|---|---|
| EP | 3 103 420 A1 | 12/2016 |
| WO | WO 92/19174 A1 | 11/1992 |
| WO | WO 2015/132406 A1 | 9/2015 |

* cited by examiner

MANDIBLE PROTRUSION SPLINT

CROSS REFERENCE TO PRIOR APPLICATIONS

This application is a U.S. National Phase application under 35 U.S.C. § 371 of International Application No. PCT/EP2018/053924, filed on Feb. 16, 2018 and which claims benefit to German Patent Application No. 10 2017 103 722.5, filed on Feb. 23, 2017. The International Application was published in German on Aug. 30, 2018 as WO 2018/153789 A1 under PCT Article 21(2).

FIELD

The present invention relates to a mandibular protrusion splint for positioning the mandible relative to the maxilla of a patient, having a maxillary splint part and a mandibular splint part, wherein two joint rods attached to the sides of the splint parts couple the two splint parts together in a movable manner. For holding the joint rods, the two splint parts have laterally, or temporarily, attached joint pins, which have a shoulder facing the splint part, a head facing away from the splint part, and a neck located between the shoulder and head, having a smaller diameter. The joint rods each have at their ends a collar which surrounds the neck of a joint pin in the mounted state, wherein the joint rod is held, via the collar, between the shoulder and the head, which each have a larger cross section than the neck.

BACKGROUND

Such a protrusion splint has previously been described, for example, in DE 20 1008 011 841 U1. EP 3 103 420 A1 and DE 10 2010 46 369 A1 also describe generic protrusion splints.

Such mandibular protrusion splints are used for the therapy of obstructive sleep apnea (OSA). By appropriate positioning of the mandible, they prevent a pathological limitation, caused by OSA, of the respiratory function during sleep. Such two-part mandibular protrusion splints having a settable therapy position—or protrusion—have been known for some time. The mechanical coupling between the maxillary splint part and the mandibular splint part is in this case implemented differently while maintaining the desired therapy position.

The two splint parts are connected together via connecting elements, which are in the form of joint rods, wherein the geometry and the mounting of the joint rods determine the degree of protrusion and have a decisive influence on the range of the possible movements of the mandible. Known mandibular protrusion splints also allow a certain range of movement for the lateral movement of the mandible, but this only corresponds to a part of the anatomically possible range of movement of the mandible. Since the actual range of movement of the mandible is greater than the range of movement allowed by the mandibular protrusion splint, high mechanical loads on the splint parts and on the patient can arise at the limits of the range of movement defined by the protrusion splint. These loads can damage the splint and in the worst case injure the patient.

SUMMARY

An aspect of the present invention is to provide a mandibular protrusion splint which, while having a simple structure and high wearing comfort, affords a great deal of breakage resistance and therefore considerably reduces the risk of injuries.

In an embodiment, the present invention provides a mandibular protrusion splint for positioning a mandible relative to a maxilla of a patient. The mandibular protrusion splint includes a maxillary splint part comprising a joint pin which is laterally attached to the maxillary splint part, a mandibular splint part comprising a joint pin which is laterally attached to the mandibular splint part, and joint rods configured to couple the maxillary splint part and the mandibular splint part together in a movable manner. The joint pin of the mandibular protrusion splint comprises a shoulder facing the maxillary splint part, a head facing away from the maxillary splint part, and a neck arranged between the shoulder and head, a cross section of each of the shoulder and the head being larger than a cross section of the neck. The joint pin of the mandibular protrusion splint comprises a shoulder facing the mandibular splint part, a head facing away from the mandibular splint part, and a neck arranged between the shoulder and head, a cross section of each of the shoulder and the head being larger than a cross section of the neck. Each joint pin is configured to hold one of the joint rods. The joint rods each comprise a collar arranged at each of their respective ends. Each collar is configured to surround the neck of one of the joint pins in a mounted state. Each of the joint rods are thereby held between the shoulder and the head. At least one of the collars of the joint rods and the head of the joint pins comprise a designed-in flexibility which, upon an excessive application of a laterally directed force exerted via one of the joint rods, initially allows a yielding movement of the joint rod and then allows the collar to slip over the head of the joint pin without being destroyed.

BRIEF DESCRIPTION OF THE DRAWINGS

The present invention is described in greater detail below on the basis of embodiments and of the drawings in which.

DETAILED DESCRIPTION

Figure 1:
FIG. 1 shows a mandibular protrusion splint in the mouth of a patient.

A key aspect of the present invention resides in a designed-in flexibility in the collar of the joint rod and/or designed-in flexibility in the head of the joint pin, which, upon excessive lateral force application, results in one of the components yielding so that, in an extreme case, the joint rod can disengage with its collar passing over the head of the joint pin without being destroyed. This function is in particular supported by a special shaping of the head of the joint pin and/or by the choice of the material thereof. Excessive lateral force application is in particular understood as meaning those forces which would cause conventional protrusion splints to be destroyed and which are caused by movements, which, as overstretched movements, lie at the limits of what is anatomically possible.

The present invention provides for a quasi two-stage yielding to be realized, wherein the joint rod is guided over the joint pin so that, in the event of lateral force application, it first of all escapes from the path of movement of the other splint part in a reversible yielding movement. Upon the application of further force beyond the end of the reversible yielding movement, the joint rod disengages over the head of the joint pin without being destroyed via the collar widening somewhat and slipping over the head of the joint pin and/or in that a part of the head yields, in particular in the region of the rear head, on account of its material or shape.

The stages are also dependent on the individual adaptation of the protrusion splint to the patient's anatomy. The splint parts thereby ideally move on a horizontal surface that is defined via the contact faces of the splint parts. Depending on the anatomy, the splint parts can tilt out of the plane in the event of extreme movements. When such a tilting occurs, the overload can ultimately no longer be prevented by a yielding movement of the joint rod since the latter, in spite of the yielding movement, is still in the range of movement of the other splint part. The overload in such extreme cases is relieved by the disengagement of the joint rod, thereby avoiding the destruction of the protrusion splint.

In an embodiment of the mandibular protrusion splint according to the present invention, the mechanical coupling can, for example, be implemented via two joint rods that act as connecting elements, one on each side. Each joint rod is assigned a receiving element in the form of an in particular integrally formed joint pin on the maxillary and the mandibular splint part.

The joint pins keep the joint rods movably in position. They are subdivided into three parts, namely, the head, the neck, and the shoulder. The shoulder and the neck can, for example, be configured in a rotationally symmetric manner with respect to the axis of the joint pin, wherein the shoulder forms the transition from the neck to the splint part. The neck is the central part of the joint pin, which forms the actual receptacle for the joint rod, wherein the mounted joint rod encloses the neck with a collar formed at its end. The neck of the joint pin is followed toward the outside by the head, which, upon normal use of the protrusion splint, prevents the joint rod from slipping off the joint pin. The joint rod has, at each end, a collar in the form of a cutout therefor, through which the joint pin projects in the mounted state. The collar advantageously forms a clearance in the form of a slot. The diameter of the cutout in the collar is dimensioned so that, in the starting state, it is less than the diameter of the head of the joint pin, thereby preventing any disengagement without expansion of the collar of the joint rod.

The flexibility according to the present invention advantageously results from the material, or material pairing, from which the parts of the protrusion splint are manufactured. The flexibility is supported by the shaping of the joint pin inasmuch as sliding and bearing faces are created that initially cause the joint rod to tilt and then the collar to slowly expand. In an embodiment of the present invention, the two splint parts with the joint pins integrally formed thereon can in this case be manufactured, for example, from a material that is harder than that of the joint rod, in particular from plastic, for example, from PMMA. The splint parts are ideally manufactured in a manner personalized to the patient and rest immovably on the teeth of the jaw. The two joint rods attached laterally by the joint pins can, for example, be manufactured from a less hard material than the splint parts, advantageously also from a plastic, for example, a polyamide. The claimed flexibility thus resides in the joint rod, the collar of which widens to a certain degree upon excessive loading so that the joint pin can disengage. The shape of the joint pin additionally provides that the joint rod can carry out the yielding movement along the joint pin in that the rounded shape at the transition from neck to head guides the joint rod and does not block it.

Excessive loading arises when a jaw movement of the patient in particular exceeds the lateral limits of the range of movement defined by the mandibular protrusion splint. While either the joint pin or the joint rod would break in such a situation in known protrusion splints, such overloading for the protrusion splint according to the present invention merely results in a yielding movement of the joint rod out of the range of movement or in reversible decoupling of the joint pin and joint rod.

The configuration according to the present invention or as a result of the specific geometry of the splint parts with their joint pins and the connecting elements in the form of joint rods, with which the two splint parts are connected, results in overloading being reversibly dampened, and the protective mechanism according to the present invention protects the protrusion splint from being destroyed, and thus the patient from being injured, in the event of an overload.

In an embodiment of the present invention, the head of the joint pin is, for example, not formed in a rotationally symmetric manner. The asymmetric head of the joint pin ideally has a raised front head and a flat rear head so that a sort of hook shape is produced. The flat rear head in this case faces the respectively other splint part. The advantages of the geometry of the joint pin according to the present invention reside in the resultant behavior of the entire connecting mechanism of the protrusion splint upon lateral loading caused by a sideways movement of the mandible executed by the patient. According to the present invention, the loading to the patient anatomy, which results, for example, in tooth loosening or damage to the mandibular joints and/or to the chewing muscles, can be avoided. A defect in the protrusion splint caused by a collision between the splint parts and the connecting element as a result of a yielding movement of the connecting element can also be reduced and thus overloading prevented.

The mandibular protrusion splint according to the present invention is described in greater detail below under reference to FIGS. 1-6.

FIG. 1 shows a mandibular protrusion splint, which is worn between the toothed maxilla 1 and the toothed mandible 4 of a patient. Both the maxillary splint part 2 and the mandibular splint part 3 are molded in a manner personalized to the patient's teeth. The maxillary splint part 2 is connected to the mandibular splint part 3 in a movable manner only via two laterally attached joint rods 5 and 6 (only the ends of which are shown for FIG. 6). The length of the joint rods 5 and 6 is used to set the protrusion of the mandible inasmuch as the mandible is prevented from moving backward by the joint rods 5 and 6. In order to hold the joint rods 5 and 6, the two splint parts have laterally, or temporarily, integrally formed joint pins 7, which pass into the collars 8, provided in the joint rods 5, in the form of slots. As a result of the slots, the two splint parts 2 and 3 are in particular able to move in a sagittal direction.

Figure 2:
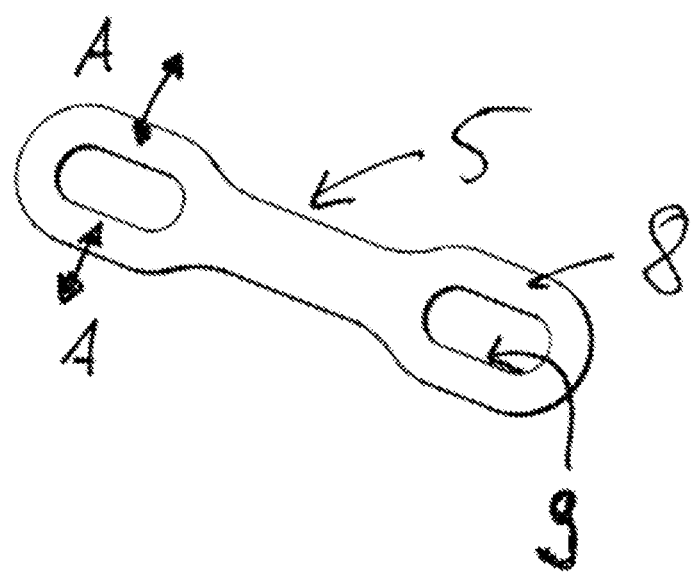
FIG. 2 shows a joint rod of a mandibular protrusion splint.

FIG. 2 shows an individual joint rod 5 having a solid central part and having collars 8 that are provided at the ends which are formed as slots. The joint rod 5 is molded in one piece from a polyamide and dimensioned so that the collars 8 have a degree of flexibility in the direction of the arrows A. The opening of the slot can accordingly widen reversibly when the collar slips over the flat rear head of the joint pin.

Figure 3:
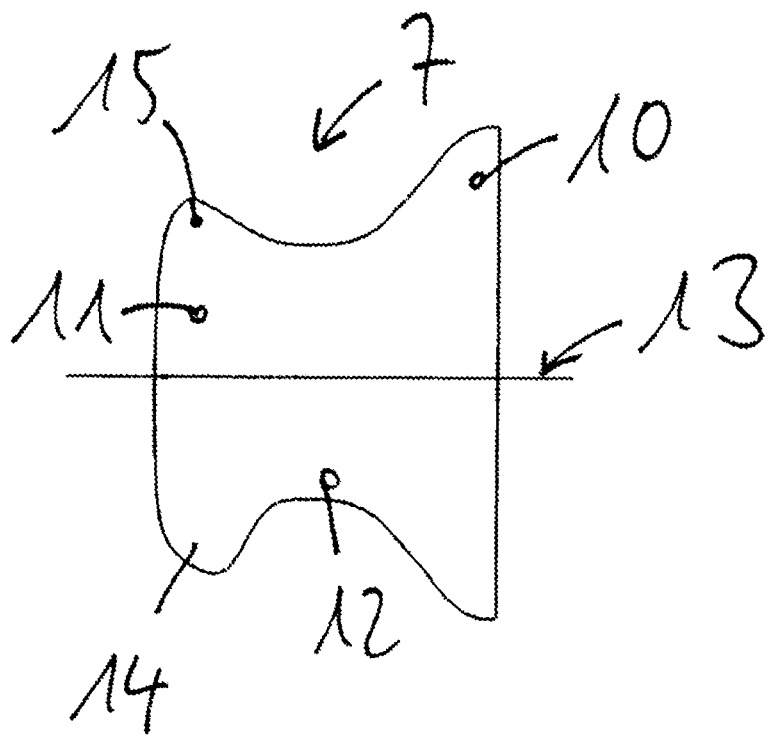
FIG. 3 shows a section through the head of a joint pin.

FIG. 3 shows a section through a joint pin 7, which is integrally formed on the splint part (not illustrated) via a shoulder 10. Facing away from the splint part, the joint pin 7 has a head 11 so that a neck 12 is formed between the shoulder 10 and head 11, the neck 12 having a smaller diameter than the shoulder 10 and head 11 with respect to an axis 13. As is apparent, the head 11 of the joint pin 7 is asymmetric and forms a protruding front head 14 and a flat rear head 15. As can be seen from FIGS. 4-6, the flat rear head 15 faces the respectively other splint part—in this case the maxillary splint part 2. As is likewise apparent from FIGS. 3-6, the contacting faces of the joint pin 7 and of the collar 8 of the joint rod 5 are formed as edge-free sliding faces.

In the mounted state, the collar 8 surrounds the neck 12 of a joint pin, wherein the joint rod 5 is held between the shoulder 10 and the head 11, which each have a larger cross section than the neck 12.

The manner in which the joint rod is mounted according to the present invention on the joint pin can be described as follows with reference to FIGS. 4-6.

Since the mandibular protrusion splint has a design that is personalized to the patient, the position of the joint pins 7 on the corresponding splint parts differs from patient to patient. Depending on the situation, it may become necessary to position the joint pin 7 at different heights on the outer edge of the splint parts.

Figures 4, 5, 6:
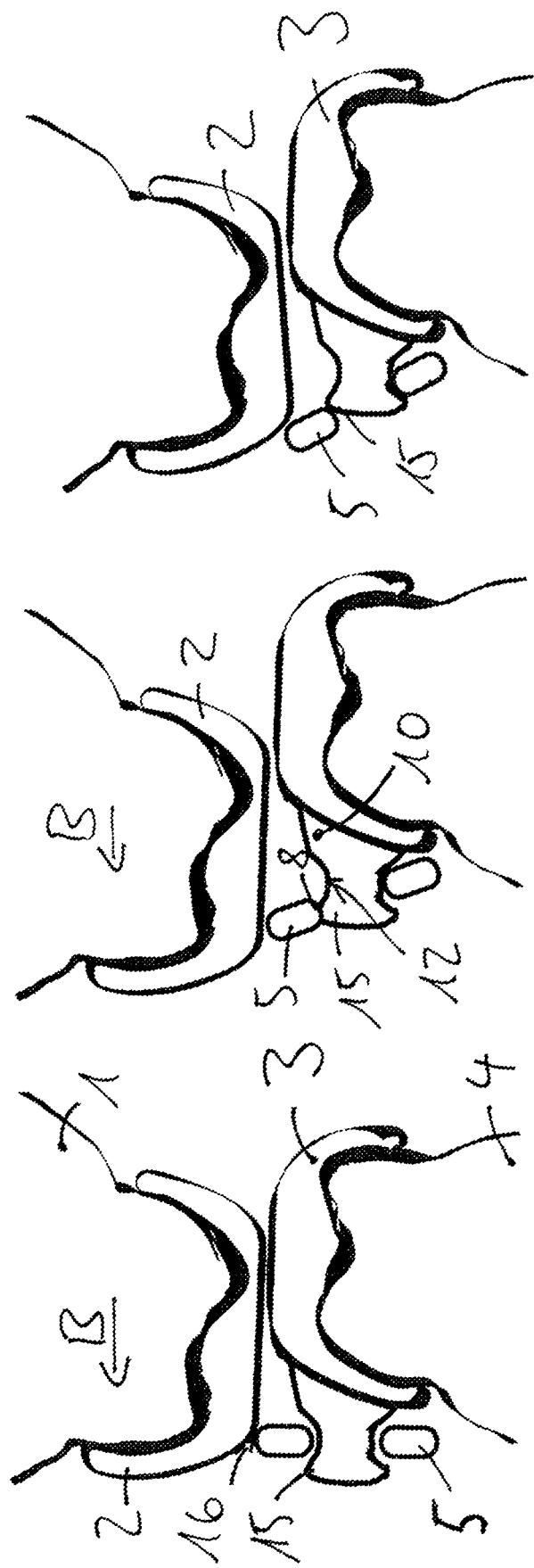
FIG. 4 shows a section in the wearing situation in the normal state.
FIG. 5 shows a section in the wearing situation in the loaded state following a yielding movement.
FIG. 6 shows a section in the wearing situation in the disengaged state.

FIG. 4 shows the situation in which the patient moves their toothed maxilla 1 excessively to the side in the direction of the arrow B and the opposite maxillary splint part 2 passes into the trajectory of the joint rod 5 so that the maxillary splint part 2 collides with the joint rod 5 at the point 16.

If the toothed maxilla 1 continues to move in this direction (arrow B), as in FIG. 5, in spite of the collision, the particular design of the transition from the shoulder 10 to the asymmetric head 11 via the neck 12 causes the joint rod 5 to tilt and one side of the collar 8 at first to bear against the shoulder 10 on the side of the projecting front head 14, while the other side of the collar 8 butts against the flat rear head 15. The joint rod 5 thus moves out of the direction of movement of the other splint part, thereby avoiding an overload. If the other splint part moves back again (counter to arrow B), the joint rod 5 straightens up; the function of the protrusion splint is not further impaired.

In this case, the inclination movement is realized by the asymmetrically designed head 11, in particular by the flat portion of the transition from neck 12 to head 11, wherein the flat portion, and thus the flat rear head 15, of the joint pins is located in each case on the side facing the opposite splint. Compared to the center of the neck 12, the flat rear head 15 is, however, elevated so that the distance of the outer edge of the flat rear head 15 from the axis of the opposite splint part is greater than the size of the radius of the neck 12. This elevation consequently has a larger cross section than the collar 8, and so, in the event of a continued inclination movement of the joint rod 5, a reversible mechanical expansion of the collar 8 occurs, which results in a damping effect on the force exerted by the opposite jaw.

If the loading by the opposite splint part, caused, for example, by tilting out of the horizontal plane of the protrusion plane, exceeds the mechanical deformation, as in FIG. 6, so that it is greater than the force brought about by the plastic deformation of the joint rod 5, at the highest point of the flat rear head 15, the joint rod 5 moves over the head 11 of the joint pin 7, thereby preventing damage to the splint part or injury to the patient. The maxillary splint part 2 is thereby decoupled from the mandibular splint part 3, at least on this side.

The two aspects, namely, the possible yielding movement of the joint rod equipped with a flexible collar out of the trajectory of the opposite splint including the undamaged return movement of the joint rod into the original orientation and the lifting of the joint rod off the joint pin in the event of an overload without damaging the protrusion splint or injuring the patient, distinguish the solution of the present invention from previously described mandibular protrusion splints.

The present invention is not limited to embodiments described herein; reference should be had to the appended claims.

What is claimed is:

1. A mandibular protrusion splint for positioning a mandible relative to a maxilla of a patient, the mandibular protrusion splint comprising:
   a maxillary splint part comprising a joint pin which is laterally attached to the maxillary splint part, the joint pin comprising a shoulder facing the maxillary splint part, a head facing away from the maxillary splint part, and a neck arranged between the shoulder and head, a cross section of each of the shoulder and the head being larger than a cross section of the neck, and a transition from the neck to the head comprising a rounded shape;
   a mandibular splint part comprising a joint pin which is laterally attached to the mandibular splint part, the joint pin comprises a shoulder facing the mandibular splint part, a head facing away from the mandibular splint part, and a neck arranged between the shoulder and head, a cross section of each of the shoulder and the head being larger than a cross section of the neck; and
   joint rods configured to couple the maxillary splint part and the mandibular splint part together in a movable manner,
   wherein,
   each joint pin is configured to hold one of the joint rods,
   the joint rods each comprise a collar arranged at each of their respective ends, each collar being configured to surround the neck of one of the joint pins in a mounted state, each of the joint rods thereby being held between the shoulder and the head,
   at least one of the collars of the joint rods and the head of the joint pins comprise a designed-in flexibility which, upon an excessive application of a laterally directed force exerted via one of the joint rods, initially allows a yielding movement of the joint rod and then allows the collar to slip over the head of the joint pin without being destroyed,
   the yielding movement of the joint rod is further allowed by the rounded shape of the joint pin at the transition from the neck to the head, the rounded shape being configured to guide the joint rod and not to block the joint rod, and
   the head of each of the joint pins is formed in an asymmetric manner so as to comprise a raised front head and a flat rear head as seen with respect to an axis which bisects the joint pin from the head to the shoulder.

2. The mandibular protrusion splint as recited in claim 1, wherein the yielding movement of the joint rod takes place in a direction of the head.

3. The mandibular protrusion splint as recited in claim 1, wherein,
   the maxillary splint part, the mandibular splint part and their respective joint pins are each manufactured from a first plastic,
   the joint rods are manufactured from a second plastic, and
   the first plastic is harder than the second plastic.

4. The mandibular protrusion splint as recited in claim 3, wherein,
   the first plastic is poly(methyl methacrylate) (PMMA), and
   the second plastic is a polyamide.

5. The mandibular protrusion splint as recited in claim 3, wherein the joint rods are manufactured via an injection molding.

6. The mandibular protrusion splint as recited in claim 1, wherein
   the flat rear head of the joint pin laterally attached to the maxillary splint part faces the mandibular splint part and the flat rear head of the joint pin laterally attached to the mandibular splint part faces the maxillary splint part.

7. The mandibular protrusion splint as claimed in claim 6, wherein,
   at least one collar of each of the joint rods is formed as a slot which is introduced into an end of the respective joint rod, and
   the slot comprises an opening which is configured to widen reversibly when slipping over the flat rear head of the joint pin.

8. The mandibular protrusion splint as claimed in claim 1, wherein a face of each of the joint pins and a face of each of the collars which contact each other are each formed as an edge-free sliding face.

* * * * *